(12) United States Patent
Nakatani et al.

(10) Patent No.: US 8,329,451 B2
(45) Date of Patent: Dec. 11, 2012

(54) CELL ELECTROPHYSIOLOGICAL SENSOR AND METHOD FOR MANUFACTURING THE SAME

(75) Inventors: Masaya Nakatani, Hyogo (JP); Hiroshi Ushio, Hyogo (JP); Soichiro Hiraoka, Osaka (JP); Akiyoshi Oshima, Osaka (JP)

(73) Assignee: Panasonic Corporation, Osaka (JP)

( * ) Notice: Subject to any disclaimer, the term of this patent is extended or adjusted under 35 U.S.C. 154(b) by 911 days.

(21) Appl. No.: 11/914,685

(22) PCT Filed: Apr. 12, 2007

(86) PCT No.: PCT/JP2007/058047
§ 371 (c)(1),
(2), (4) Date: Nov. 16, 2007

(87) PCT Pub. No.: WO2007/119772
PCT Pub. Date: Oct. 25, 2007

(65) Prior Publication Data
US 2009/0081765 A1    Mar. 26, 2009

(30) Foreign Application Priority Data

Apr. 14, 2006 (JP) ................ 2006-111767
May 29, 2006 (JP) ................ 2006-148063

(51) Int. Cl.
*C12M 1/00* (2006.01)
*C12M 1/42* (2006.01)
*C12M 3/00* (2006.01)
*C12M 1/34* (2006.01)

(52) U.S. Cl. .............. 435/285.2; 435/288.7; 435/283.1; 435/285.1; 435/288.5

(58) Field of Classification Search ............... 435/288.7, 435/283.1–309.4
See application file for complete search history.

(56) References Cited

U.S. PATENT DOCUMENTS

| | | | |
|---|---|---|---|
| 5,874,668 A * | 2/1999 | Xu et al. | 73/105 |
| 2003/0113833 A1 * | 6/2003 | Oka et al. | 435/29 |
| 2004/0197898 A1 * | 10/2004 | Nakatani et al. | 435/287.1 |
| 2004/0252867 A1 * | 12/2004 | Lan et al. | 382/124 |

FOREIGN PATENT DOCUMENTS

| | | | |
|---|---|---|---|
| GB | 2358513 A * | 7/2001 | |
| JP | 2002-508516 A | 3/2002 | |
| WO | WO 99/31503 | 6/1999 | |
| WO | WO 2005/001018 A1 | 1/2005 | |

OTHER PUBLICATIONS

International Search Report for International Application No. PCT/JP2007/058047 dated Jul. 17, 2007.

* cited by examiner

*Primary Examiner* — Nathan Bowers
*Assistant Examiner* — Lydia Edwards
(74) *Attorney, Agent, or Firm* — RatnerPrestia

(57) ABSTRACT

In a cell electrophysiological sensor having a thin plate with a through hole, a support plate with a through hole and a container plate with a through hole stuck to an upper portion of this support plate, the support plate and the container plate are stuck to each other through fusion with a portion of the outer shape of a first electrode in a ring shape intervening in a portion of the interface. In this configuration, a cell electrophysiological sensor which allows for measurement with high precision can be attained, and a manufacturing method which is excellent in terms of mass production can be provided.

20 Claims, 12 Drawing Sheets

US 8,329,451 B2

CELL ELECTROPHYSIOLOGICAL SENSOR AND METHOD FOR MANUFACTURING THE SAME

This Application is a U.S. National Phase Application of PCT International Application PCT/JP2007/058047.

TECHNICAL FIELD

The present invention relates to a cell electrophysiological sensor for measuring the phenomenon of cell electrophysiology, such as the potential within the cells or the potential outside the cells which is used in order to measure the physicochemical change that occurs as a result of the activity of the cells, and a method for manufacturing the same.

BACKGROUND ART

Conventional patch clamping methods in electrophysiology have been known as the methods for measuring the ion channel in a cell membrane, and various functions of the ion channel have been clarified in accordance with these patch clamping methods. The functions of the ion channel are of a great interest in cytology, and these are applied to the development of medicines. Meanwhile, since the patch clamping methods in the technology for measurement require an extremely high level of skill such that a minute micropipette is inserted into one cell with high precision, a skilled worker is required, and thus, the methods are inappropriate methods in the case where measurement is required with a high throughput.

Therefore, a plate type probe has been developed using a microscopic processing technology. This probe does not require the insertion of a micropipette into an individual cell, and therefore, is appropriate for an automated system. A hole is provided in a carrier for separating two regions, for example, so that an electrical field is generated using electrodes installed above and below this carrier, and thus, the hole of the cell is efficiently maintained and an electrical measurement is carried out between the upper and lower electrodes so that an electrophysiological measurement of the cell is made possible. This has such an advantage that a through hole formed in the plate functions in the same manner as the hole at the end of a glass pipette so that the electrophysiological phenomenon of a cell can be recorded with high precision, and at the same time, the cell can be automatically attracted in accordance with such a method as suction from the rear surface side of the plate, and thus, the cell can be easily held. This technology is described in, for example, Patent Document 1. It is understood that in this conventional configuration, however, many measurement processes can be carried out at once by forming a number of sensors, but no configurations of the sensor members relating to the measurement with high precision and ease of manufacture are disclosed.

[Patent Document 1] Japanese Translation of PCT Unexamined Patent Publication No. 2002-508516

DISCLOSURE OF THE INVENTION

The present invention provides a cell electrophysiological sensor having: a thin plate with a through hole; a support plate with a through hole; and a container plate with a through hole stuck to an upper portion of this support plate, wherein the support plate and the container plate are fused and stuck to each other through the stuck interface where a material for absorbing or reflecting heat, light or infrared rays is formed in a portion or in the entire area. In this configuration, a cell electrophysiological sensor for measurement with high precision can be attained and a manufacturing method which is excellent in terms of mass production can be provided.

PREFERENCE MARKS IN THE DRAWINGS

Figure 1:
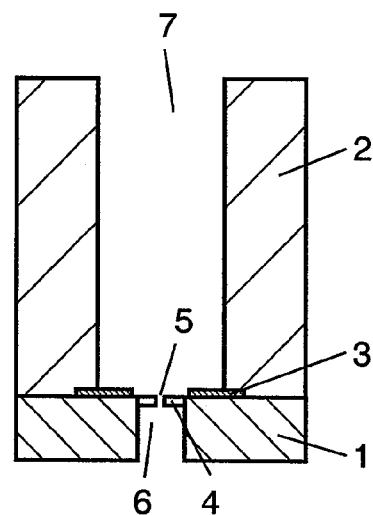
FIG. 1 is a cross sectional diagram showing a cell electrophysiological sensor according to the first embodiment of the present invention.

1 Support plate
2 Container plate
3 Electrode
4 Thin plate
5 First through hole
6 Second through hole
7 Third through hole
8 Trench
9 Opening
10 First pigment
11 Second pigment
12 Laser beam with first wavelength
13 Laser beam with second wavelength
14 Condenser lens
15 Laser beam
16 Flat Fresnel lens
18 Flow path plate
19 Laser beam

PREFERRED EMBODIMENTS FOR CARRYING OUT OF THE INVENTION

In the following, the cell electrophysiological sensor and the method for manufacturing the same according to the present invention are described in reference to the drawings. As for the symbols used in the respective drawings, the same symbols are attached to components which are the same. The respective drawings are schematic and the dimensions are not shown with precision on a reduced scale.

First Embodiment

Figure 2:
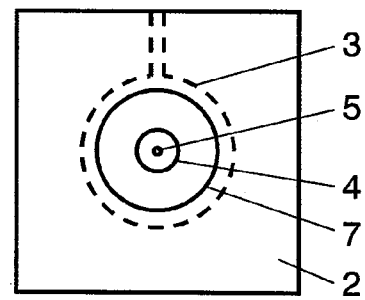
FIG. 2 is a top diagram showing the cell electrophysiological sensor according to the first embodiment of the present invention.

FIG. 1 is a cross sectional diagram showing a cell electrophysiological sensor according to the first embodiment of the present invention, and FIG. 2 is a top diagram showing the same. The main components of the cell electrophysiological sensor according to the first embodiment are support plate 1 made of a resin, container plate 2 made of a resin and thin plate 4 made of silicon. First through hole 5, second through hole 6 and third through hole 7 are formed in thin plate 4, support plate 1 and container plate 2, respectively. As shown in FIG. 2, electrode 3 in a ring shape is formed around second through hole 6 in support plate 1. This electrode 3 is made of a material made of copper, aluminum, nickel, titanium, gold, silver, platinum or silver chloride, or a complex body or layered body of these materials. This electrode 3 is in such a form as to cover the entirety of the periphery of the opening of third through hole 7 in the bottom portion of container plate 2. The outer shape of electrode 3 in a ring shape is sandwiched and stuck between support plate 1 and container plate 2. In this configuration, sticking can be completed in such a state that the form of third through hole 7 in the vicinity of thin plate 4 is maintained with high precision. Thin plate 4 is held and stuck inside second through hole 6 in support plate 1, and the regions above and below support plate 1 are connected only through first through hole 5 of thin plate 4.

In this configuration, the cell electrophysiological sensor according to the present invention can be attained as a cell electrophysiological sensor having members integrally formed with high precision, including third through hole 7, which becomes a container portion for storing a fluid, such as a chemical or a culture fluid, and thin film 4 in which first through hole 5 for holding electrode 3 and cells is formed. That is to say, electrode 3 intervenes in the stuck interface between support plate 1 and container plate 2, and thus, the temperature for fusing this portion is lowered when support plate 1 and container plate 2 are stuck through fusion, so that the form of third through hole 7 in the vicinity of electrode 3 can be maintained with high precision. Thus, portions of container plate 2 and support plate 1 can be prevented from deforming and the space above thin plate 4 can be prevented from being closed.

In addition, electrode 3 is sandwiched between container plate 2 and support plate 1 so as to be firmly stuck, and thus, the fluid stored in the container can be prevented from accidentally leaking out, making precise measurement possible.

Furthermore, in this configuration, the cell electrophysiological sensor can be manufactured efficiently in the case where support plate 1 and container plate 2 are fused through heating, in particular fused through heating using laser beam 19 (described in detail below in the manufacturing method). In this case, when either support plate 1 or container plate 2 is made of a material that can be fused through heating, any material may be combined as the other material. Combinations, for example glass with glass, glass with a resin material, or a resin material with a resin material, are possible. From among these, a combination of a resin material with a resin material is particularly preferable for fusion through heating, from the point of view of productivity. In addition, in the case where container plate 2 is made of a resin material which absorbs at least laser beam 19 so as to emit heat and support plate 1 is made of a resin material which allows laser beam 19 to transmit, support plate 1 and container plate 2 can be stuck through fusion by irradiating the support plate 1 side with laser beam 19. According to this configuration, a cell electrophysiological sensor which is excellent in terms of mass production can be attained.

As the resin material which allows laser beam 19 to transmit, transparent resin materials are generally preferable, and polystyrene, polyethylene, polycarbonate polyolefin, acryl resins and the like can be used. Meanwhile, materials which absorb laser beam 19 can be attained by mixing a material which absorbs laser beam 19 well, such as a pigment, carbon black, an inorganic oxide or the like, into a resin. That is to say, a material which allows laser beam 19 to transmit and a material having such properties as to absorb laser beams so as to emit heat can be attained, even when the same material is used for the bases. By using these properties, support plate 1 and container plate 2, for example, can be formed of the same material so as to have the coefficient of expansion, and thus, a cell electrophysiological sensor having excellent durability against changes in temperature can be attained. Conversely, support plate 1 and container plate 2 may be formed as a combination of resin materials having different properties, and thus, it is also possible to attain a cell electrophysiological sensor having excellent reliability in terms of resistance to heat and resistance to chemicals.

More preferably, support plate 1 may be made of a transparent material and electrode 3 may be formed of such a material as a precious metal, for example platinum, gold or silver, a base metal, for example aluminum, copper, titanium or nickel, or silver chloride. Electrode 3 may be made of an electrode material selected from among mixed bodies and layered bodies of these. In addition, particularly in the case where electrode 3 has the configuration of a layered electrode, the electrode material of which the surface makes contact with support plate 1 may have shine, like copper, aluminum, nickel, titanium, gold, silver and platinum. As a result, laser beam 19 can be well controlled, as described below, in the case where the lower side of support plate 1 is irradiated with laser beam 19 for fusion through heating using laser beam 19, and therefore, efficient production is made possible.

Furthermore, it is preferable for the thickness of electrode 3 to be no less than 5 µm. As a result, a more efficient manufacturing method for a cell electrophysiological sensor can be provided, as described below.

Next, the manufacturing method for a cell electrophysiological sensor according to the present first embodiment is described in reference to the drawings. FIGS. 3 to 9 are cross sectional diagrams illustrating the manufacturing method for a cell electrophysiological sensor according to the present first embodiment.

Figure 3:
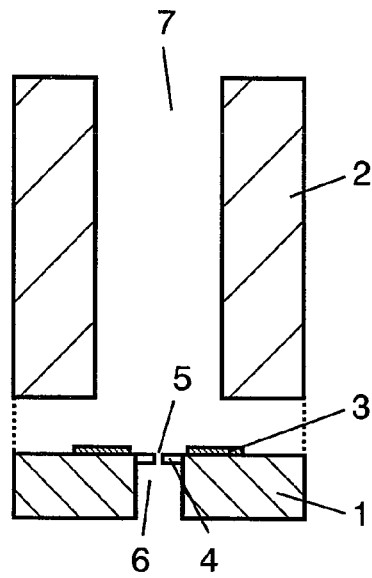
FIG. 3 is a cross sectional diagram illustrating a manufacturing method according to the first embodiment of the present invention.

As shown in FIG. 3, thin plate 4 in which first through hole 5 is formed, is inserted into second through hole 6 in support plate 1 so as to be held and stuck. This thin plate 4 is formed of such a material as silicon or silicon dioxide, and at least one or more first through holes 5 are provided in advance. As the method for forming these first through holes 5, a conventional processing means, such as photolithography, etching or laser processing, is used. Electrode 3 is formed on the upper surface of support plate 1. An appropriate electrode material for this electrode 3 is selected from among electrode materials which include any one of copper, aluminum, nickel, titanium, gold, silver, platinum and silver chloride, and layered bodies of these.

Figure 4:
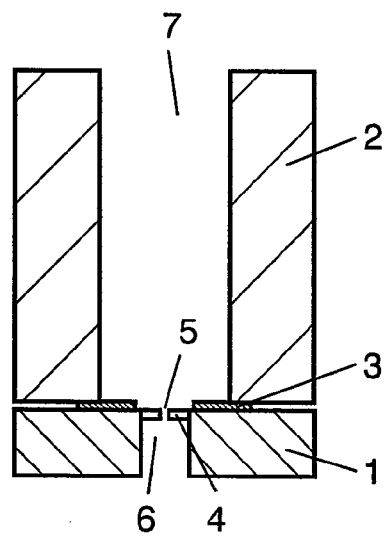
FIG. 4 is a cross sectional diagram illustrating the manufacturing method according to the first embodiment of the present invention.

Next, as shown in FIG. 4, support plate 1 and container plate 2 are layered on top of each other. At this time, they are aligned so that electrode 3 in a ring shape on support plate 1 covers a portion of the bottom of container plate 2 around third through hole 7. That is to say, the electrode comes inside the periphery of third through hole 7. In addition, electrode 3 has a thickness of no less than 5 µm, and therefore, the thickness of electrode 3 causes a slight gap to be formed between support plate 1 and container plate 2, as shown in FIG. 4.

Figure 5:
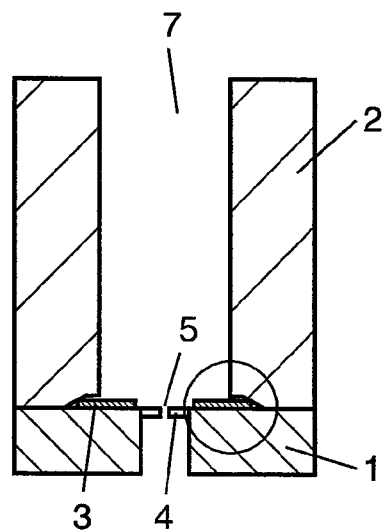
FIG. 5 is a cross sectional diagram illustrating the manufacturing method according to the first embodiment of the present invention.
Figure 6:
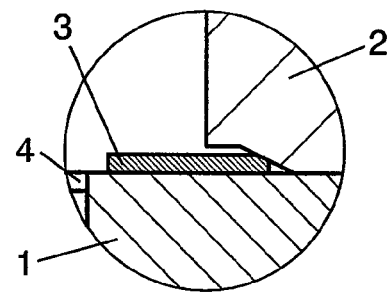
FIG. 6 is a cross sectional diagram showing an enlarged main portion illustrating the manufacturing method according to the first embodiment of the present invention.
Figure 8:
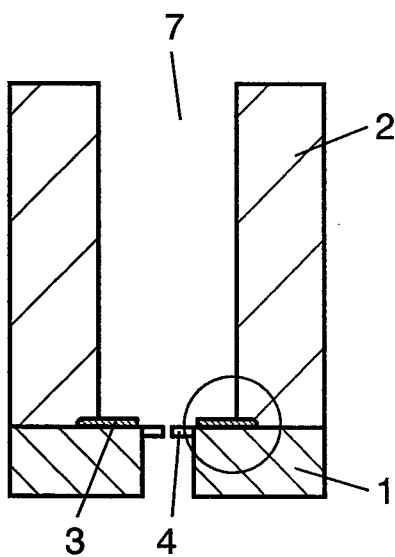
FIG. 8 is a cross sectional diagram illustrating the manufacturing method according to the first embodiment of the present invention.
Figure 9:
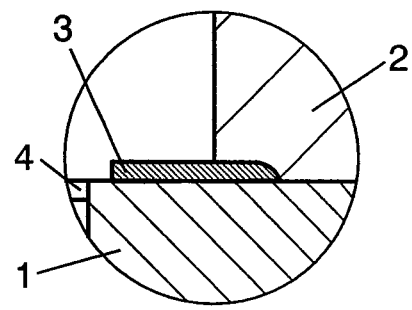
FIG. 9 is a cross sectional diagram showing an enlarged main portion illustrating the manufacturing method according to the first embodiment of the present invention.

Next, as shown in FIG. 5, when pressure is applied from the top and bottom of support plate 1 and container plate 2, there is distortion at the bottom of container plate 2. An enlargement of the portion surrounded by the circle of FIG. 5 is shown in FIG. 6. The gap portion between container plate 2 and support plate 1 is closed, so that the two make contact with each other, and a microscopic gap is formed above electrode 3. When the lower portion of support plate 1 is irradiated with laser beam 19 so as to be heated in this state, the resin in the portion which makes contact with the plate is softened and fused so that the formed gap is filled in for firm adhesion, as shown in FIG. 8 and FIG. 9, which is a diagram showing an enlargement of the portion surrounded by the circle in FIG. 8.

Here, electrode 3 is formed in a ring shape so as to cover a portion of third through hole 7, and therefore, container plate 2 in the vicinity of electrode 3 is heated at a relatively low temperature. Therefore, the resin ingredient does not melt unnecessarily. That is to say, container plate 2 does not melt and flow out unnecessarily, closing third through hole 7 and electrode 3.

In addition, as shown in FIG. 6, it is more advantageous for a gap to be formed in the vicinity of electrode 3. This makes it difficult for heat to be conducted toward container plate 2 and prevents the resin from excessively liquidating.

Thus, support plate 1 is preferably made of a material which is transparent to visible light of 800 to 1000 nm and container plate 2 is colored by mixing in a material which absorbs laser beam 19, such as a pigment or carbon black. Furthermore, as the method for heating support plate 1 and container plate 2, the support plate 1 side is irradiated with laser beam 19 having, for example, a wavelength of 800 to 1000 nm, a power for irradiation of approximately 10 to 20 W and a spot diameter of 2 to 5 mm. As a result, it is possible to concentratedly heat in a portion in the vicinity of the interface between container plate 2 and support plate 1, and thus, it is possible to fuse and stick only the interface between support plate 1 and container plate 2.

Figure 7:
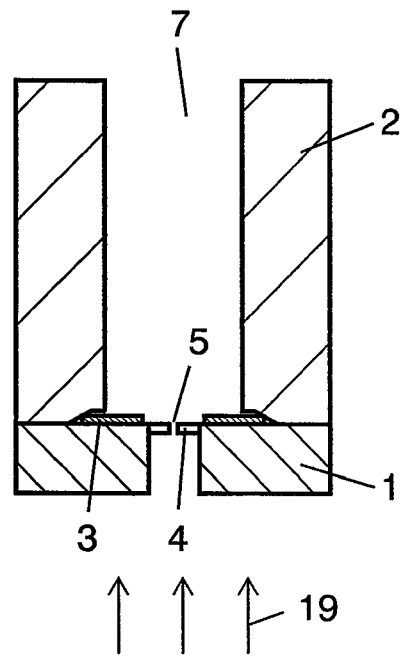
FIG. 7 is a cross sectional diagram illustrating the manufacturing method according to the first embodiment of the present invention.

Furthermore, it is preferable for electrode 3 to include any one of copper, aluminum, nickel, titanium, gold, silver and platinum as the main ingredient at least in the portion in which the surface makes contact with support plate 1. In this configuration, as shown in FIG. 7, when the lower side of support plate 1 is irradiated with laser beam 19, laser beam 19 transmits through support plate 1 and is absorbed by colored container plate 2. Then, the portion of container plate 2 which is irradiated starts melting and fuses with support plate 1 on the side, as show in FIGS. 8 and 9. Here, electrode 3 in a ring shape is formed so as to cover third through hole 7 in container plate 2, and electrode 3 has shine on the surface on the support plate 1 side, and therefore, efficiently reflects laser beam 19 so as to prevent the periphery of third through hole 7 in container plate 2 from being heated unnecessarily. Accordingly, the amount which liquates from this portion is small, and the liquated resin does not flow into third through hole 7 or toward electrode 3 in such a manner as to close these.

In addition, in the case where support plate 1 and container plate 2 are formed of a resin, the thickness of the electrode may be no less than 5 µm, and thus, better effects as those described above can be gained.

Here, in terms of the type of laser beam 19, the wavelength, the power and the spot diameter are not limited to those in the above description, and other wavelengths, powers, and spot diameters may be selected, as long as they allow the laser beam to transmit through support plate 1 and heat container plate 2 appropriately as described above. In terms of the spot diameter, for example, laser beam 19 may be focused not in a circle but in line form or surface form. In these cases, many regions can be heated at once, and therefore, it is possible to shorten the time for processing.

Second Embodiment

Figure 10:
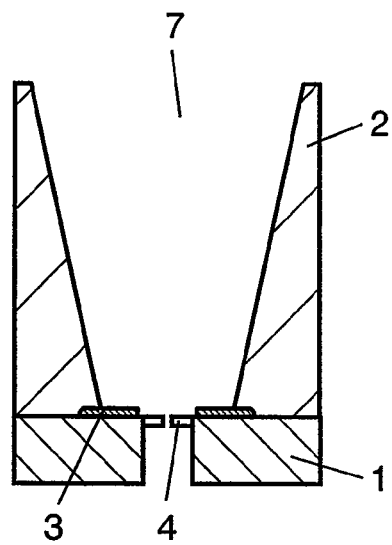
FIG. 10 is a cross sectional diagram illustrating a manufacturing method according to the second embodiment of the present invention.
Figure 11:
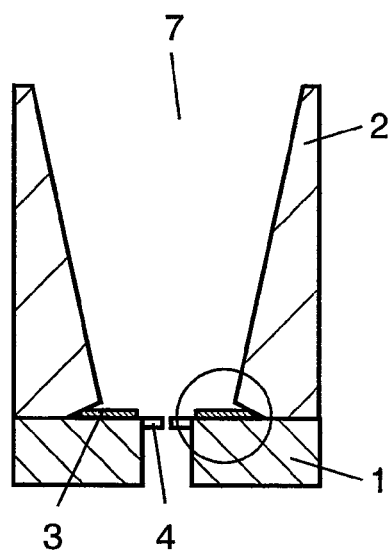
FIG. 11 is a cross sectional diagram illustrating the manufacturing method according to the second embodiment of the present invention.
Figure 12:
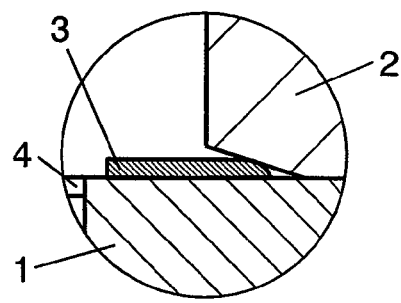
FIG. 12 is a cross sectional diagram showing an enlarged main portion illustrating the manufacturing method according to the second embodiment of the present invention.

FIG. 10 is a cross sectional diagram showing the cell electrophysiological sensor according to the second embodiment of the present invention. According to the first embodiment, third through hole 7 has a penetrating form whose inner diameter is consistent. According to the second embodiment, third through hole 7 is in a tapered form wherein the hole becomes smaller towards support plate 1. FIG. 11 is a cross sectional diagram illustrating the manufacturing method according to the second embodiment of the present invention. FIG. 12 is a cross sectional diagram showing an enlarged main portion illustrating the manufacturing method according to the second embodiment. According to the second embodiment, the same manufacturing method as in the first embodiment is carried out. That is to say, when pressure is applied from the top and the bottom of support plate 1 and container plate 2, there is distortion at the bottom of container plate 2. FIG. 11 shows a cross sectional diagram at this time, and FIG. 12 shows an enlarged portion surrounded by the circle in FIG. 11. The resin that forms container plate 2 is thin in the vicinity of the bottom of third through hole 7, and therefore, when pressure is applied to container plate 2 and support plate 1, a gap is formed in an upper portion of electrode 3 without fail. As a result, it becomes more difficult for the heat resulting from the irradiation with laser beam 19 to be conducted so that the amount of the resin that forms container plate 2 and which accidentally liquates can further be reduced. As described above, a cell electrophysiological sensor in which container plate 2 and support plate 1 are stuck to each other with high precision, thereby making measurement with high precision possible, and a manufacturing method for the same can be implemented.

Third Embodiment

In the following, the cell electrophysiological sensor and the manufacturing method for the same according to the third embodiment of the present invention are described in reference to the drawings.

Figure 13:
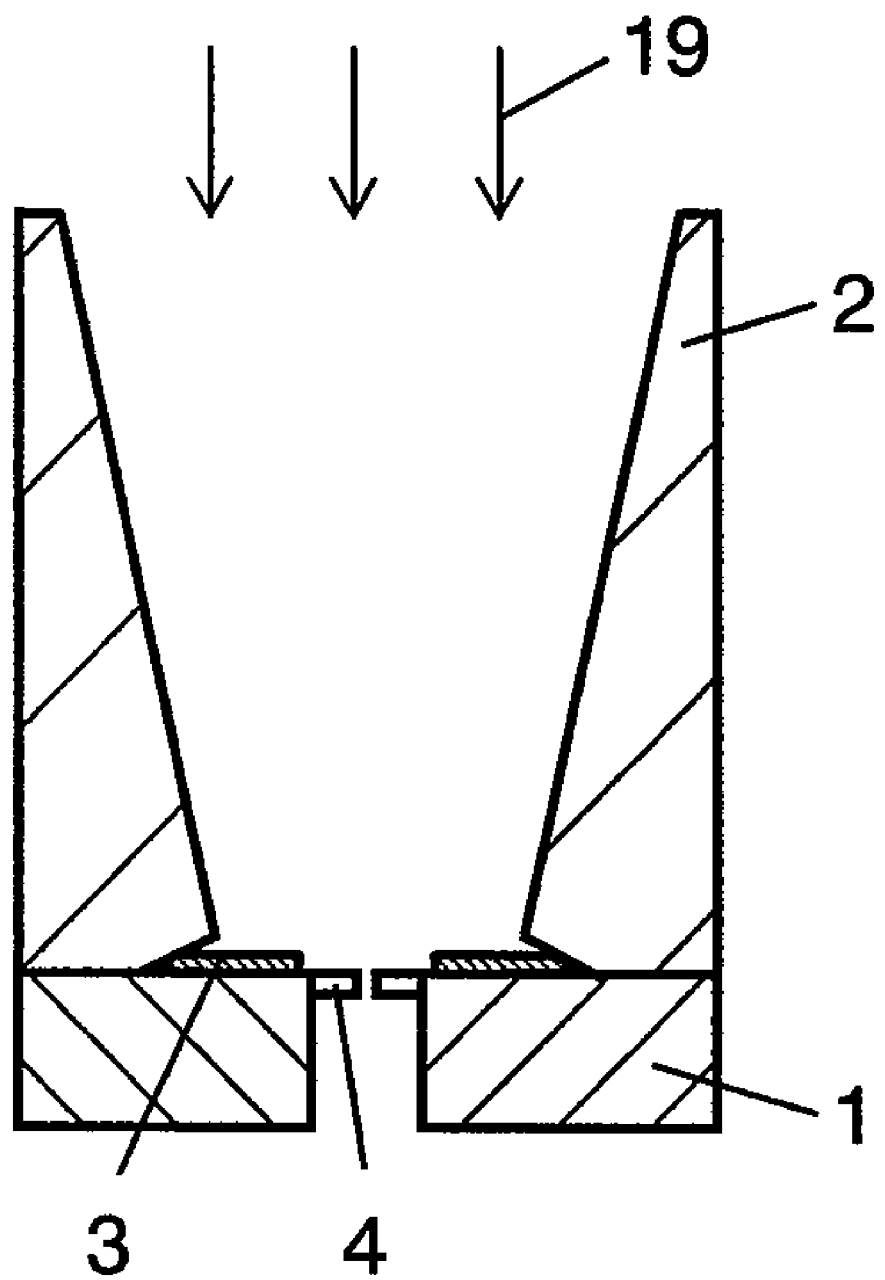
FIG. 13 is a cross sectional diagram illustrating a manufacturing method according to the third embodiment of the present invention.

FIG. 13 is a cross sectional diagram showing the cell electrophysiological sensor according to the third embodiment of the present invention. The points, which are different from the first embodiment, are that container plate 2 is transparent to laser beam 19 and color is put into support plate 1 so that support plate 1 is heated by laser beam 19. The first and second embodiments disclose a manufacturing method according to which the support plate 1 side is irradiated with laser beam 19. According to the third embodiment, the container plate 2 side, which is the opposite side, is irradiated with laser beam 19 so that container plate 2 and support plate 1 are fused and stuck to each other.

In this case, it is preferable for the portion of electrode 3 of which the surface makes contact with the side of container plate 2 to be formed of any electrode material from among copper, aluminum, nickel, titanium, gold, silver and platinum. These electrode materials have shine, and thus, reflect laser beam 19 efficiently so that the portion of support plate 1 in the vicinity of second through hole 6 can be prevented from being excessively heated. As a result, the resin is not melted to such a degree that the portion of the resin in the vicinity of second through hole 6 is accidentally changed in form, and thus, the problem such that the liquate resin closes first through hole 5 can be solved.

Fourth Embodiment

Figure 14:
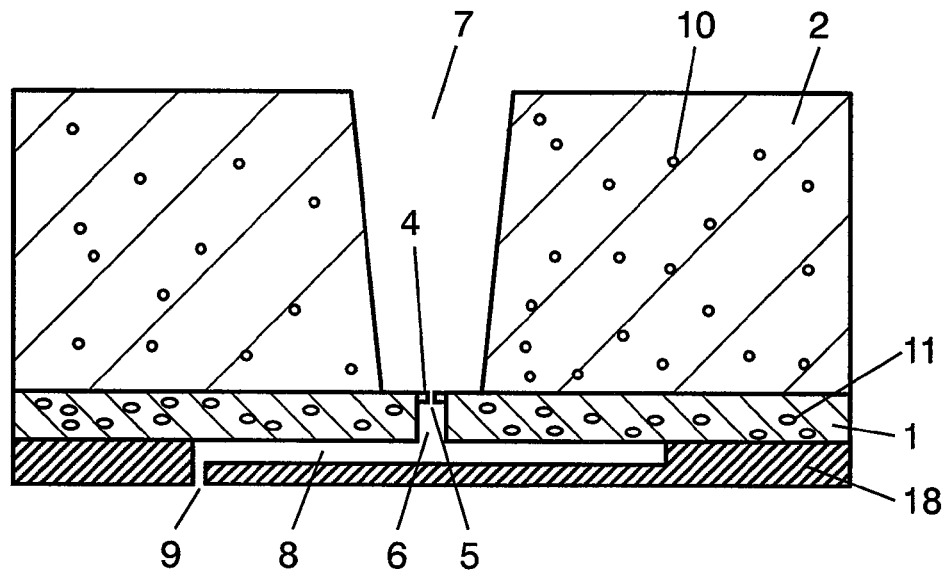
FIG. 14 is a cross sectional diagram showing a cell electrophysiological sensor according to the fourth embodiment of the present invention.

FIG. 14 is a cross sectional diagram showing the cell electrophysiological sensor according to the fourth embodiment of the present invention. As shown in FIG. 14, the cell electrophysiological sensor according to the fourth embodiment is formed of container plate 2 made of a first thermoplastic resin having third through hole 7, support plate 1 made of a second thermoplastic resin having second through hole 6, which is fused and stuck to the lower side of this container plate 2, a flow path plate 18 made of a third thermoplastic resin having a trench 8, which is fused and stuck to the lower side of this support plate 1, and a thin plate 4 of which the main ingredient is silicon and which has first through hole 5 inside the above described second through hole 6. Thin plate 4 is held and stuck inside second through hole 6 in support plate 1, and space regions above and below this support plate 1 are connected only through first through hold 5 in thin plate form in the configuration. Flow path plate 18 having trench 8 is stuck to support plate 1. A closed space is formed inside flow path plate 18, and opening 9 is formed so as to be connected to this closed space, and thus, a predetermined fluid, such as a chemical or a culture fluid, can be introduced into or sucked out from the closed space.

In addition, this configuration may have at least one first through hole 5, one second through hole 6, one third through hole 7 and one trench 8, respectively. However, it is also possible to forme a number of first through holes 5, a number of second through holes 6, a number of third through holes 7 and a number of trenches 8.

In the cell electrophysiological sensor formed as described above, a container portion for storing a fluid, such as a culture fluid, in an upper portion of thin plate 4, thin plate 4 for holding cells in first through hole 5 and a flow path portion for storing a fluid or making a fluid flow into and flow out from a lower portion of this thin plate 4 are members of the cell electrophysiological sensor which are integrated with each other.

Here, in the case where container plate 2, support plate 1 and flow path plate 18 are all formed of a thermoplastic resin, these members become excellent in uniformity and can be firmly stuck to each other using a fusing technique. In addition, a fluid stored in the container portion or the flow path portion does not leak out because of a deficit in the adhesion. The space regions above and below thin plate 4 are connected only through second through hole 6 formed in the thin plate, and therefore, a cell electrophysiological sensor, which makes precise measurement of the cell electrophysiological phenomenon possible, can be attained.

Figure 15:
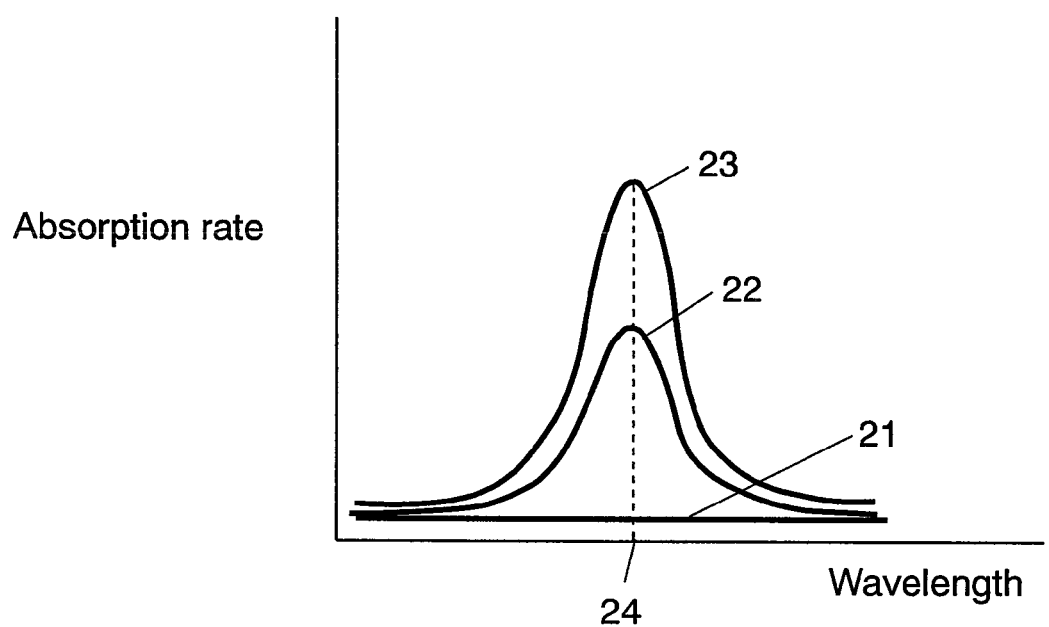
FIG. 15 is a schematic graph showing light absorption curves for specific wavelengths of the forming material according to the fourth embodiment of the present invention.

Furthermore, the light absorbing regions of the thermoplastic resins for container plate 2, support plate 1 and flow path plate 18 in the cell electrophysiological sensor according to this embodiment are selected in a planned way. That is to say, the cell electrophysiological sensor is characterized by being formed so that the absorption rates become smaller in the order of first thermoplastic resin 23 forming container plate 2, second thermoplastic resin 22 forming support plate 1 and third thermoplastic resin 21 forming flow path plate 18. That is to say, the entire area of the interface between container plate 2 and support plate 1 is formed of a material which absorbs heat, light or infrared rays. FIG. 15 schematically shows the manner how the absorption rates of the respective thermoplastic resins are different for light having specific wavelength 24, and as shown in FIG. 15, first thermoplastic resin 23 forming container plate 2 has the highest absorption rate for light having specific wavelength 24, second thermoplastic resin 22 forming support plate 1 has a smaller absorption rate and third thermoplastic resin 21 of flow path plate 18 has the smallest absorption rate, and thus, the absorption ratios become smaller in the order of the first, second and third thermoplastic resins in the configuration. In the above described configuration, the three plates are firmly stuck without inconsistency in fusion, thereby providing high reliability.

Figure 16:
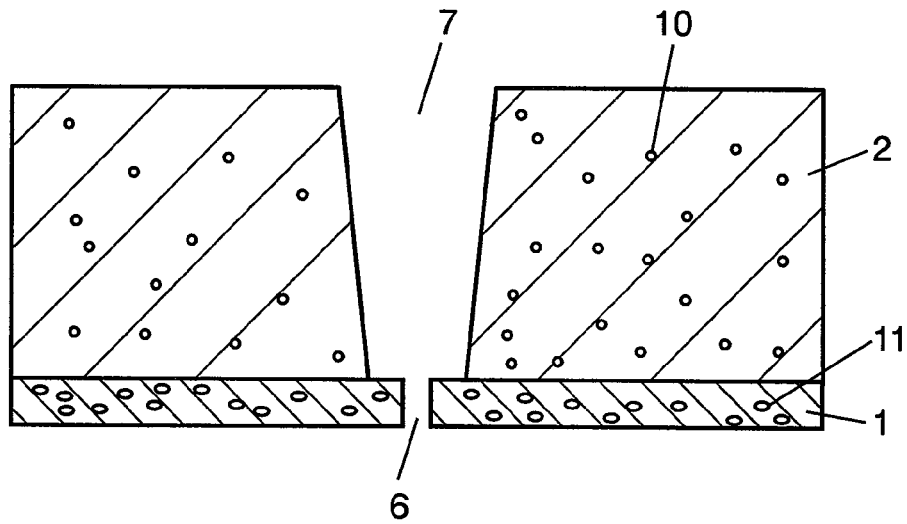
FIG. 16 is a cross sectional diagram illustrating the manufacturing method according to the fourth embodiment of the present invention.

In the following, the above description is described in further detail following the order of the manufacturing process. FIGS. 16 to 20 are cross sectional diagrams illustrating the manufacturing method according to the fourth embodiment of the present invention. First, as shown in FIG. 16, container plate 2 made of the first thermoplastic resin and support plate 1 made of the second thermoplastic resin are layered on top of each other. Here, first pigment 10 is mixed in order for the first thermoplastic resin to have a higher absorption rate of light having a specific wavelength or a number of wavelengths. A material that greatly absorbs light can be used as this first pigment 10, and carbon black and the like can be cited as an example. Meanwhile, second pigment 11 is mixed in order for the second thermoplastic resin to be transparent to a certain degree and have an appropriate absorption of light. Here, the same pigment as first pigment 10 can be used for second pigment 11 of which the concentration in the mixture is lower so that the transparency can be changed. Furthermore, it is possible to use another pigment having a different absorption rate.

Figure 17:
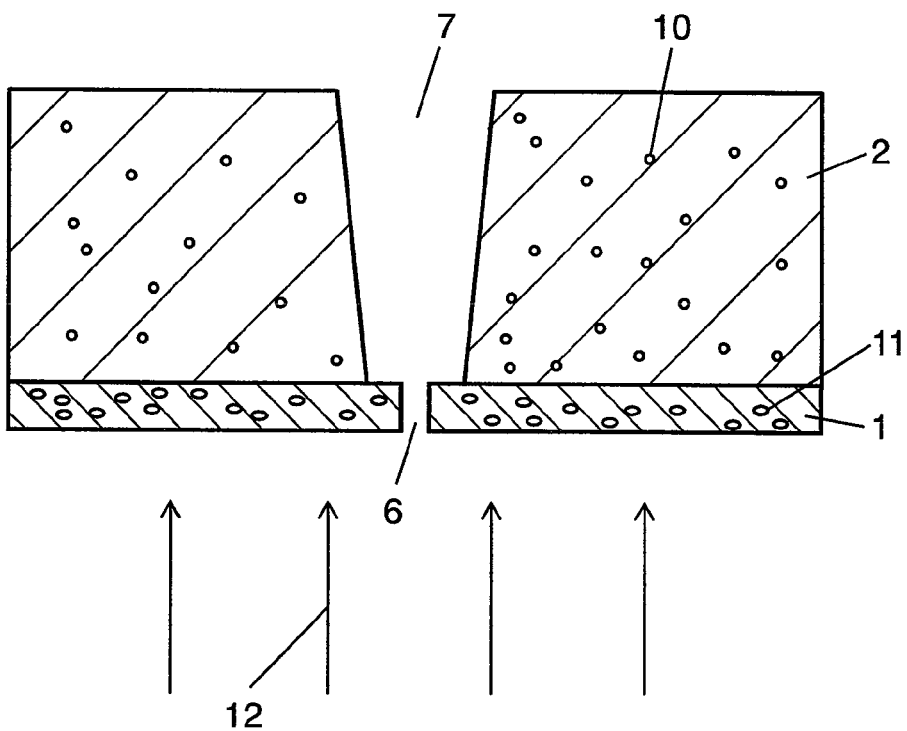
FIG. 17 is a cross sectional diagram illustrating the manufacturing method according to the fourth embodiment of the present invention.

Next, as shown in FIG. 17, the support plate 1 side is irradiated with laser beam 12 having a first wavelength, which is light having a specific wavelength. By doing so, an appropriate amount of laser beam 12 having the first wavelength transmits through support plate 1 and is efficiently absorbed in the interface between container plate 2 and support plate 1 so that the thermoplastic resin is melted and the two plates are firmly stuck to each other through fusion.

Figure 18:
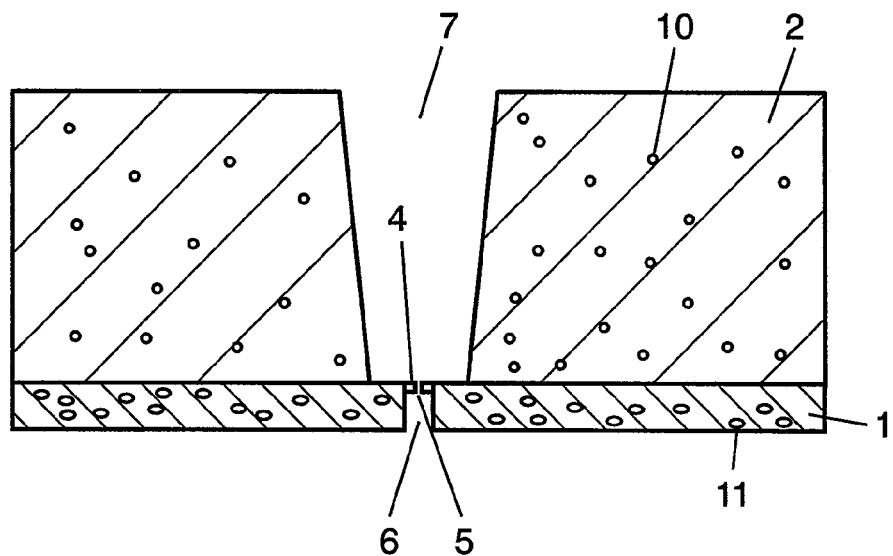
FIG. 18 is a cross sectional diagram illustrating the manufacturing method according to the fourth embodiment of the present invention.

Next, as shown in FIG. 18, thin plate 4, to which first through hole 5 has been provided in advance, is inserted into second through hole 6 in support plate 1 so as to be held and stuck.

Figure 19:
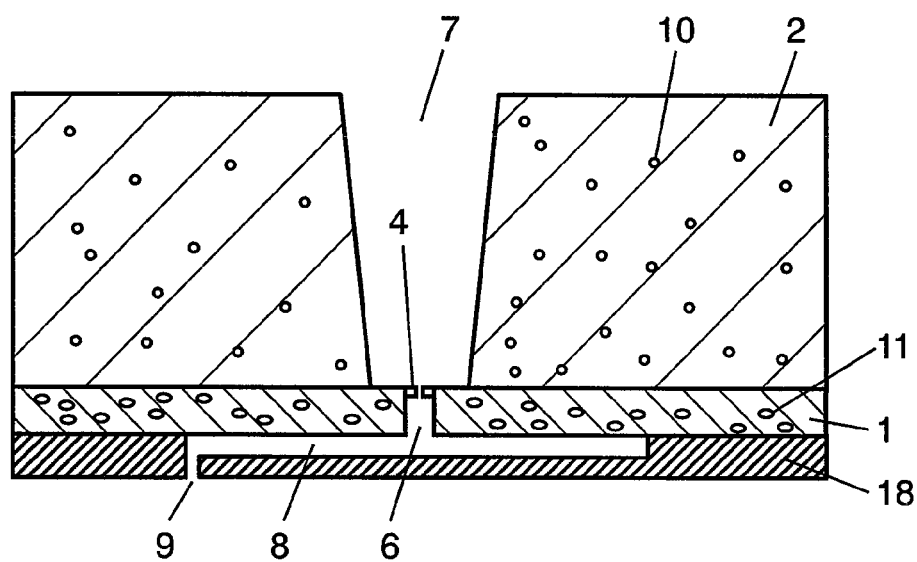
FIG. 19 is a cross sectional diagram illustrating the manufacturing method according to the fourth embodiment of the present invention.

Next, as shown in FIG. 19, flow path plate 18 made of the third thermoplastic resin in which trench 8 has been formed in advance is layered on the lower portion of support plate 1. Here, properties such that the absorption rate for light having a specific wavelength or a number of wavelengths is smaller are provided to the third thermoplastic resin. In order to do this, it is preferable to use a transparent resin which does not contain a pigment at all.

Figure 20:
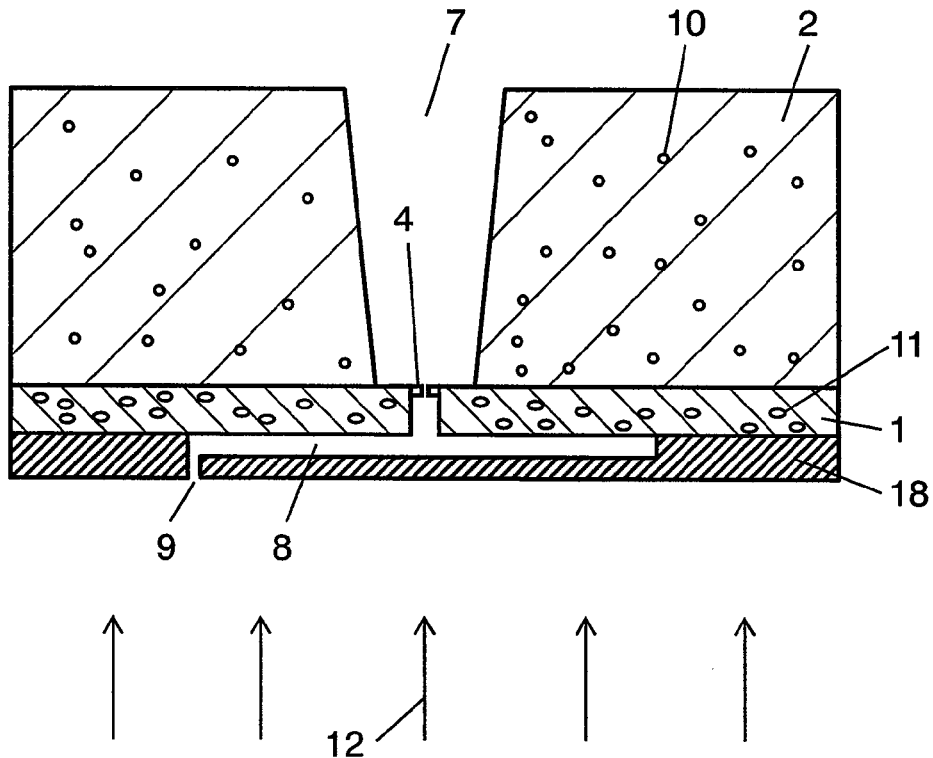
FIG. 20 is a cross sectional diagram illustrating the manufacturing method according to the fourth embodiment of the present invention.

Next, as shown in FIG. 20, the flow path plate 18 side is irradiated with laser beam 12 having the first wavelength, which is light having a specific wavelength. By doing this, laser beam 12 having the first wavelength transmits through flow path plate 18, and support plate 1 absorbs an appropriate amount of the laser beam in such a manner that light is efficiently absorbed in the interface between support plate 1 and flow path plate 18 so that the second thermoplastic resin is melted and the two plates are firmly stuck to each other.

As described above, container plate 2, support plate 1 and flow path plate 18 can be efficiently and firmly stuck together and combined without inconsistency in fusion. It was actually confirmed that the reliability of the stuck portion in the cell electrophysiological sensor fabricated so as to have the above described configuration is very high, and thus, an electrophysiological phenomenon of cells can be measured with high precision by using this cell electrophysiological sensor.

As the thermoplastic resins used herein, polyethylene, polystyrene, polycarbonate, olefin polymer and olefin copolymer, for example, are preferable. In addition, more preferably, the main ingredients of the first thermoplastic resin, the second thermoplastic resin and the third thermoplastic resin are of the same material. By doing this, reliability in the joint through fusion and productivity can further be increased.

Fifth Embodiment

Figure 21:
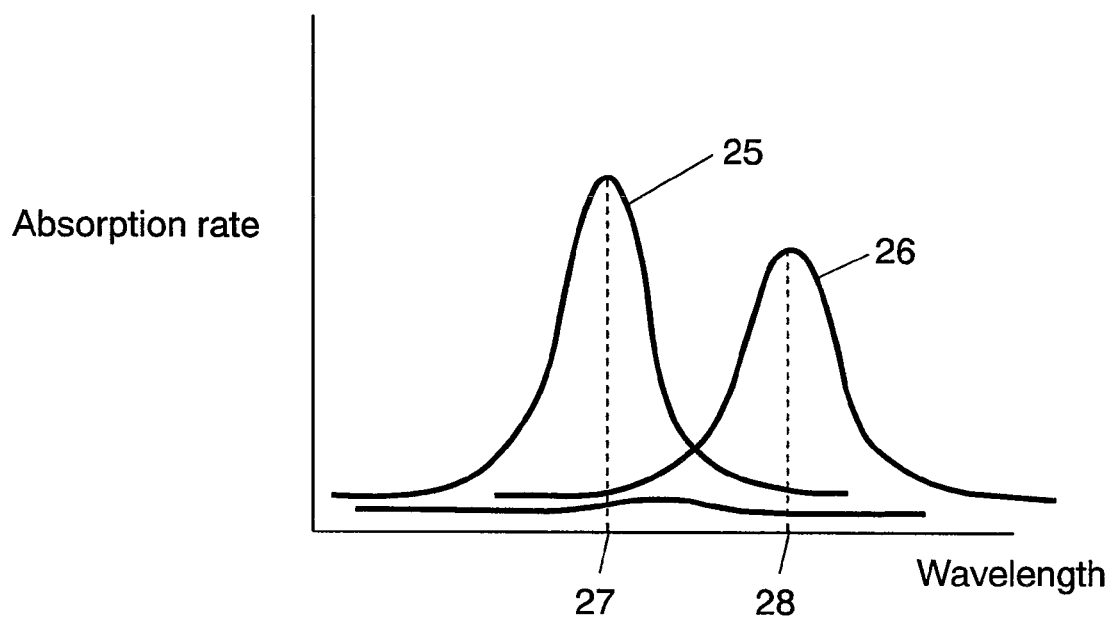
FIG. 21 is a schematic graph showing light absorption curves for a specific wavelength of the forming material according to the fifth embodiment of the present invention.

FIG. 21 is a schematic graph showing light absorption curves for a specific wavelength of the forming material according to the fifth embodiment of the present invention. As shown in FIG. 21, absorption properties 25 for light 27 having a specific first wavelength are provided to first pigment 10 contained in the first thermoplastic resin forming container plate 2, and properties 26 which allow light 27 having the first wavelength to transmit and absorb light having a second wavelength 28 which is different from the first wavelength are provided to second pigment 11 contained in the second thermoplastic resin forming support plate 1. As a result, more efficient assembly becomes possible.

Figure 22:
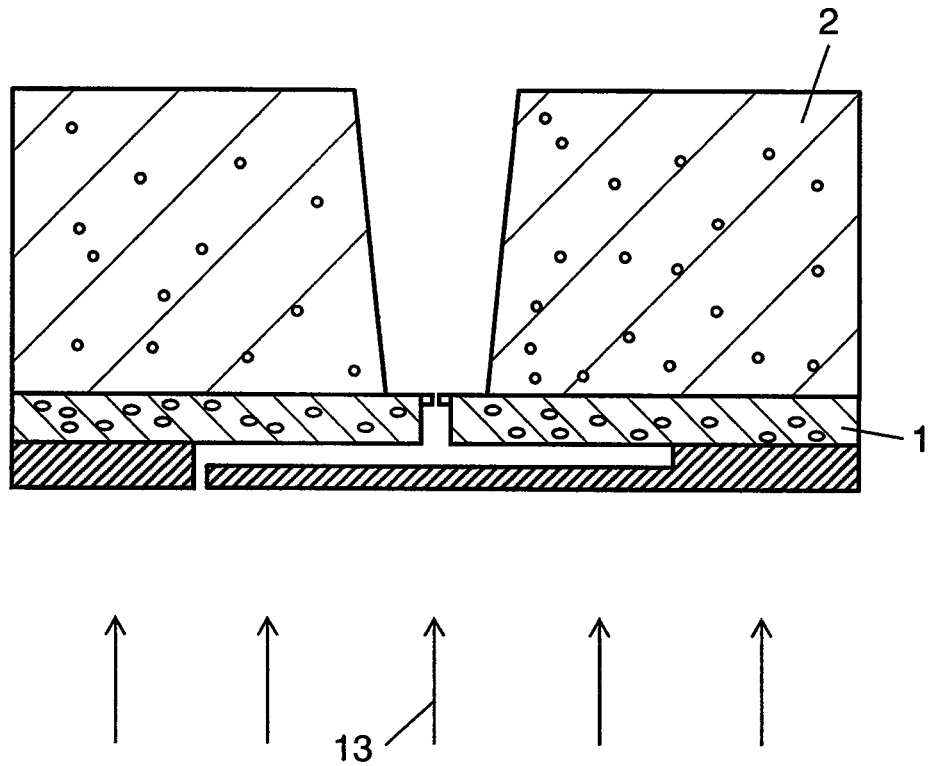
FIG. 22 is a cross sectional diagram illustrating the manufacturing method according to the fifth embodiment of the present invention.

That is to say, in the case where container plate 2 and support plate 1 are fused, the support plate 1 side is irradiated with laser beam 12 having first wavelength 27 in the same manner as shown in FIG. 16. Laser beam 12 having first wavelength 27 is not absorbed by support plate 1, and therefore, laser beam 12 can be efficiently absorbed in the interface between container plate 2 and support plate 1 so that support plate 1 and container plate 2 can be fused. Furthermore, in order for support plate 1 and flow path plate 18 to be fused, as shown in FIG. 22, the flow path plate 18 side is irradiated with laser beam 13 having second wavelength 28. Laser beam 13 with which the flow path plate is irradiated can be efficiently absorbed in the interface between support plate 1 and flow path plate 18. In addition, even in the case where support plate 1 does not entirely absorb laser beam 13 having the second wavelength and allows a slight amount to transmit, the laser beam is not absorbed by container plate 2, and therefore, unnecessary fusion or damage does not occur in the interface between container plate 2 and support plate 1. In addition, container plate 2, support plate 1 and flow path plate 18 are layered on top of each other and simultaneously irradiated with laser beams having two types of wavelengths so that they can be fused and stuck together collectively. That is to say, a manufacturing method having high productivity can be implemented.

The first wavelength is preferably 930 to 950 nm, and first pigment 10 absorbs this first wavelength well, and the second wavelength is preferably 800 to 820 nm, and second pigment 11 absorbs this second wavelength well. These wavelengths belong to a wavelength region which is generally well used, and therefore, first pigment 10 and second pigment 11 which absorb these wavelengths are easily available, and manufacturing apparatuses are also easily available, and thus, there is an advantage that production is possible with a simple manufacturing apparatus.

Here, absorption properties as described above can be provided to the thermoplastic resins, respectively, and thus, the same effects can be gained.

In addition, first pigment 10 can be provided in the interface between support plate 1 and container plate 2 in accordance with such a method as through application, and thus, the same effects can be gained. In the same manner, second pigment 11 can be provided as a pigment application layer in accordance with the same method as described above in the interface between support plate 1 and flow path plate 18, and thus, the same effects can be gained.

In addition, the laser beam having the first wavelength can be emitted from a semiconductor laser of which the center value of the wavelength is 938 nm, and the laser beam having the second wavelength can be emitted from a semiconductor laser of which the center value of the wavelength is 808 nm, and thus, the laser beam sources are easily available, and light sources having the output energy which is sufficient for fusion can be easily attained. The use of laser fusion has such effects that the residual stress can be reduced and a joint with high purity can be attained.

As first pigment 10, Clearweld (registered trademark by Gentex Corporation in the United States), which is commercially available as a pigment for laser fusion, can be used. As second pigment 11, perylene pigments and the like can be used. Here, perylene pigments are available as Lumogen (registered trademark by BASF Aktiengesellschaft), and the product types "Lumogen R IR 788" and "Lumogen R IR 765" are commercially available as the pigments for fusion with a wavelength of 808 nm.

Sixth Embodiment

Figure 23:
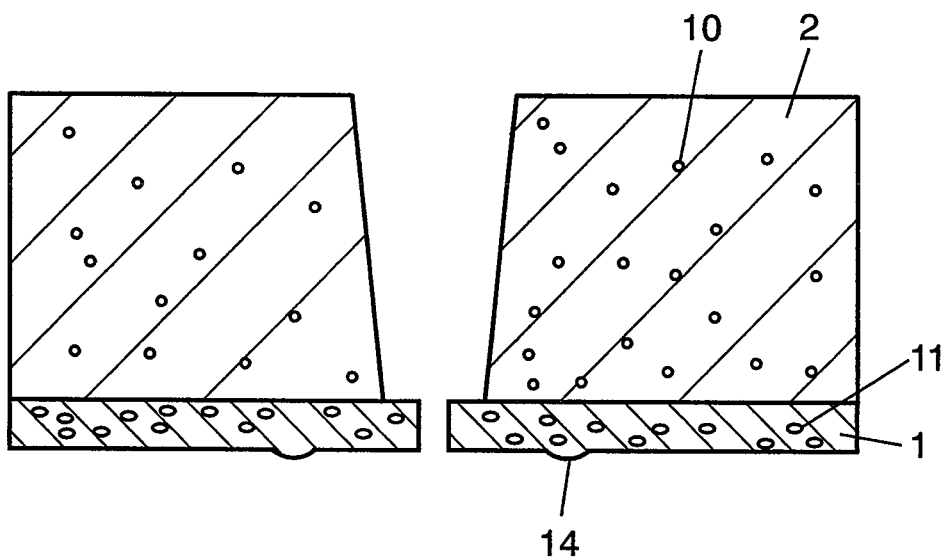
FIG. 23 is a cross sectional diagram showing a cell electrophysiological sensor according to the sixth embodiment of the present invention.
Figure 24:
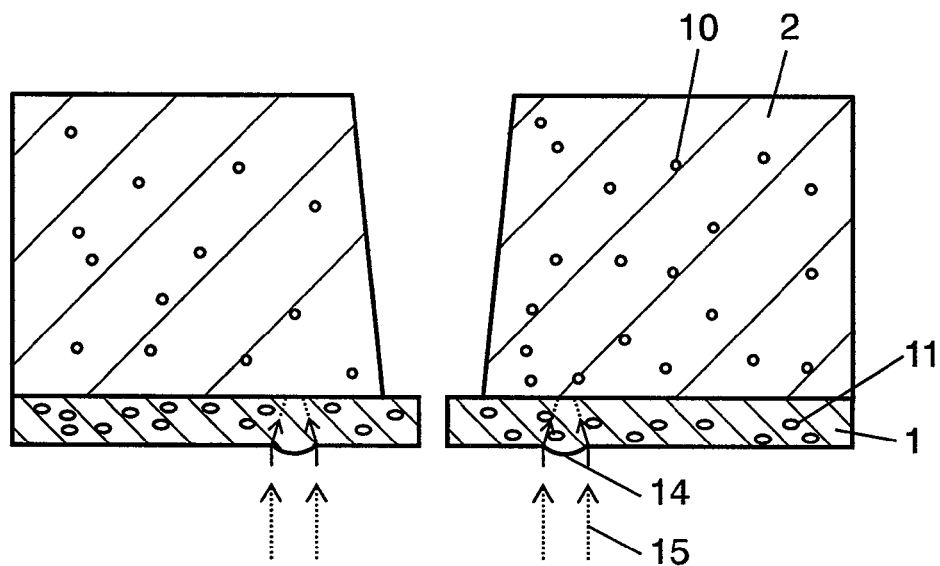
FIG. 24 is a cross sectional diagram illustrating the manufacturing method according to the sixth embodiment of the present invention.

In the following, the cell electrophysiological sensor and the manufacturing method for the same according to the sixth embodiment of the present invention are described in reference to the drawings. FIGS. 23 and 24 are cross sectional diagrams illustrating the configuration of the cell electrophysiological sensor according to the present sixth embodiment. The basic configuration is approximately the same as the configuration of the cell electrophysiological sensor according to the fourth embodiment, and the description in detail thereof is omitted.

In particular, the configuration of the cell electrophysiological sensor according to this embodiment is greatly different from the sensor structure according to the fourth embodiment in that condenser lenses 14 are formed on the surface of support plate 1 as shown in FIG. 23. As a result, as shown in FIG. 24, when the sensor is irradiated with laser beam 15, laser light 15 is condensed by condenser lenses 14 so that the light energy of laser beam 15 can be more efficiently concentrated on the interface between container plate 2 and support plate 1. As a result, portions can be stuck through laser fusion only in a location which is required to be stuck.

Furthermore, these condenser lenses 14 are formed in one line form so that the interface between container plate 2 and support plate 1 beneath the surface on which the condenser lens 14 is formed can be selectively fused through irradiation with laser beam 15 along the line where this condenser lens 14 is formed. This line formed in one line form may be either straight or curved, and thus, can be freely designed so that the region, which is required to form a flow path from which no fluid must leak, can be fused. As a result, such effects can be gained that a clean joint can be implemented and the portions can be stuck with the thermal strain restricted to a minimum.

In the case where this condenser lens 14 becomes an obstacle with regards to flatness, it is possible to remove this through polishing afterwards.

Seventh Embodiment

Figure 25:
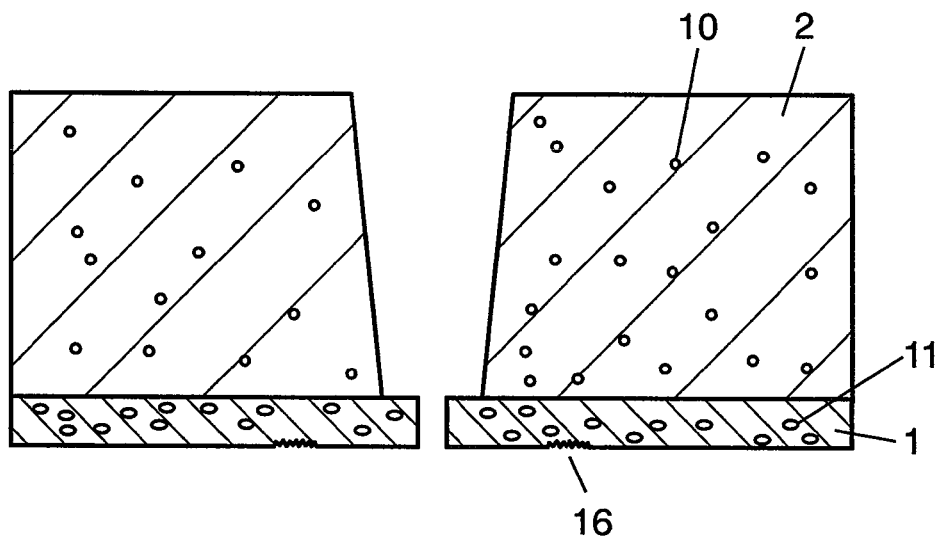
FIG. 25 is a cross sectional diagram showing a cell electrophysiological sensor according to the seventh embodiment of the present invention.

FIG. 25 is a cross sectional diagram showing the cell electrophysiological sensor according to the seventh embodiment of the present invention. Though the lenses according to the sixth embodiment have a concave form as shown in FIG. 23, the form of the lens is not limited to this, and flat Fresnel lenses 16 can also be used as shown in FIG. 25. In the case of these flat Fresnel lenses 16, a great amount of unevenness is not formed in support plate 1, and therefore, container plate 2 and support plate 1 can be layered with high precision when they are layered on top of each other.

Eighth Embodiment

Figure 26:
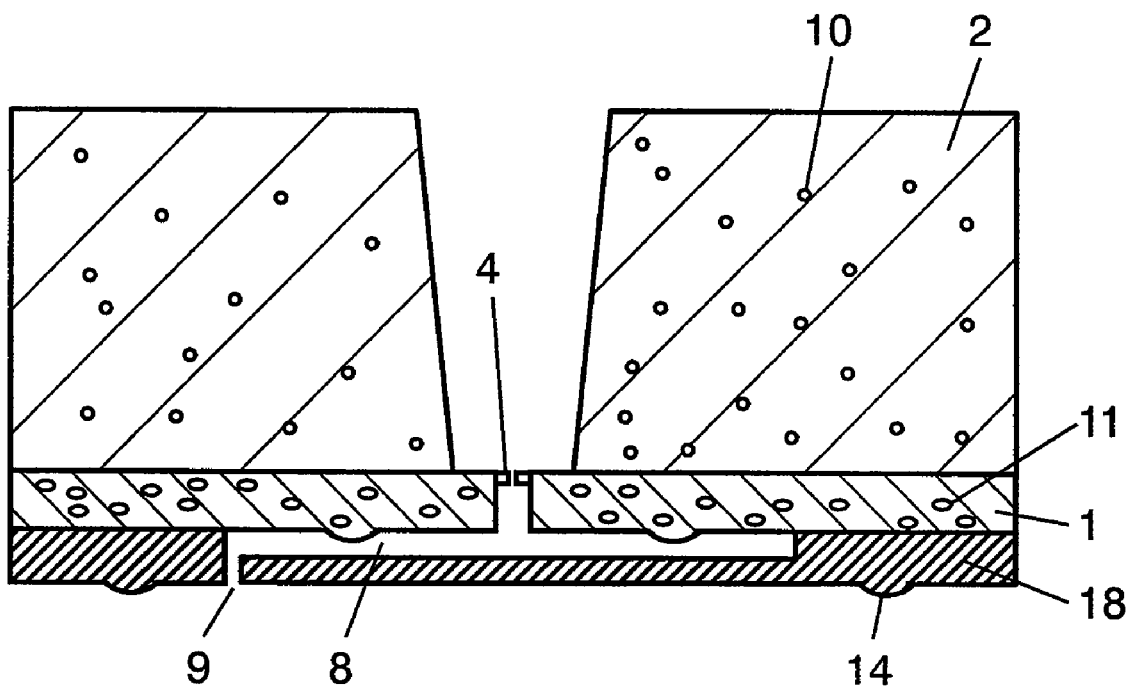
FIG. 26 is a cross sectional diagram showing a cell electrophysiological sensor according to the eighth embodiment of the present invention.

FIG. 26 is a cross sectional diagram showing the cell electrophysiological sensor according to the eighth embodiment of the present invention. As shown in FIG. 26, condenser lenses 14 are formed on the surface inside flow path plate 18 in the case where flow path plate 18 is stuck to support plate 1. As a result, flow path plate 18 can be efficiently fused to support plate 1 with high precision using laser beam 15 in accordance with the same method as described above.

INDUSTRIAL APPLICABILITY

The cell electrophysiological sensor and the method for manufacturing the same according to the present invention can allow a process for measuring cell electrophysiological properties to be carried out with high precision and make manufacture easy, and therefore, are useful for measuring equipment for chemical screening with high precision through which pharmacological effects can be determined with the cell electrophysiological phenomenon as a standard for determination.

The invention claimed is:
1. A cell electrophysiological sensor, comprising:
a thin plate with a first through hole;
a support plate with a second through hole, the thin plate being attached to an inside wall of the second through hole;
a container plate with a third through hole stuck to the support plate, and
a first electrode for absorbing or reflecting heat or reflecting light is formed between the support plate and the container plate.
2. The cell electrophysiological sensor according to claim 1, wherein the first electrode is in a ring shape and formed on the upper surface of the support plate and around the second through hole in the support plate.
3. The cell electrophysiological sensor according to claim 2, wherein the first electrode covers an opening of the third through hole in a bottom portion of the container plate.
4. The cell electrophysiological sensor according to claim 3, wherein a portion of an outer shape of the first electrode is formed in the ring shape and buried between the support plate and the container plate.
5. The cell electrophysiological sensor according to claim 4, wherein the thickness of the first electrode is no less than 5 µm.
6. The cell electrophysiological sensor according to claim 4, wherein the first electrode is an electrode including any one of copper, aluminum, nickel, titanium, gold, silver, platinum and silver chloride.
7. The cell electrophysiological sensor according to claim 1, wherein the support plate or the container plate is made of a resin material.
8. The cell electrophysiological sensor according to claim 7, wherein the support plate and the container plate are stuck to each other through laser fusion.
9. The cell electrophysiological sensor according to claim 8, wherein the support plate is made of a resin material which is transparent to a laser beam and the container plate is made of a resin material which absorbs a laser beam so as to emit heat.
10. The cell electrophysiological sensor according to claim 8, wherein the container plate is made of a resin material which is transparent to a laser beam and the support plate is made of a resin material which absorbs a laser beam so as to emit heat.
11. The cell electrophysiological sensor according to claim 1, wherein the third through hole is in a tapered form so that the inner diameter becomes smaller toward the support plate.
12. The cell electrophysiological sensor having a thin plate with a first through hole, a support plate having a second through hole, the thin plate being attached to an inside wall of the second through hole, and a container plate with a third through hole stuck to the support plate according to claim 1, further comprising a flow path plate with a trench, which is stuck to the support plate.

13. The cell electrophysiological sensor according to claim 12, wherein a main ingredient of the container plate, a main ingredient of the support plate and a main ingredient of the flow path plate are of the same thermoplastic resin material.

14. The cell electrophysiological sensor according to claim 12, wherein the container plate is made of a first thermoplastic resin, the support plate is made of a second thermoplastic resin and the flow path plate is made of a third thermoplastic resin so that the rate of absorption of light of such a wavelength as to allow light to transmit through the flow path plate by the first thermoplastic resin is lower than the rate of absorption of light by the second thermoplastic resin.

15. The cell electrophysiological sensor according to claim 12, wherein the container plate is made of a first thermoplastic resin, the support plate is made of a second thermoplastic resin and the flow path plate is made of a third thermoplastic resin so that the first thermoplastic resin contains a first pigment which absorbs light of a first wavelength and the second thermoplastic resin contains a second pigment which allows light of the first wavelength to transmit and absorbs light of a second wavelength.

16. The cell electrophysiological sensor according to claim 15, wherein the first pigment absorbs light of the first wavelength ranging from 930 nm to 950 nm and the second pigment allows light of the first wavelength to transmit and absorbs light of the second wavelength ranging from 800 nm to 820 nm.

17. The cell electrophysiological sensor according to claim 15, wherein the first pigment is provided between the support plate and the container plate.

18. The cell electrophysiological sensor according to claim 15, wherein the second pigment is provided between the support plate and the flow path plate.

19. The cell electrophysiological sensor according to claim 12, wherein a lens for condensing light is provided between the support plate and the flow path plate.

20. The cell electrophysiological sensor according to claim 12, wherein a lens for condensing light is provided on a surface of the flow path plate.

* * * * *